US006183950B1

(12) United States Patent
Madonna et al.

(10) Patent No.: US 6,183,950 B1
(45) Date of Patent: Feb. 6, 2001

(54) METHOD AND APPARATUS FOR DETECTING VIRUSES USING PRIMARY AND SECONDARY BIOMARKERS

(75) Inventors: Angelo J. Madonna, Denver; Kent J. Voorhees, Golden, both of CO (US)

(73) Assignee: Colorado School of Mines, Golden, CO (US)

( * ) Notice: Under 35 U.S.C. 154(b), the term of this patent shall be extended for 0 days.

(21) Appl. No.: 09/130,207

(22) Filed: Aug. 4, 1998

Related U.S. Application Data

(60) Provisional application No. 60/094,838, filed on Jul. 31, 1998.

(51) Int. Cl.[7] .............................. C12Q 1/70; G01N 31/00
(52) U.S. Cl. .................................................. 435/5; 436/71
(58) Field of Search .................................... 435/5; 436/71

(56) References Cited

U.S. PATENT DOCUMENTS

| | | | |
|---|---|---|---|
| 5,469,369 | 11/1995 | Rose-Pehrsson et al. | 364/497 |
| 5,550,062 | 8/1996 | Wohltjen et al. | 436/155 |

OTHER PUBLICATIONS

Marple, V.A. et al., Aerosol Sample Acquisition for Chemical and Biological Agent Detection, Abstract, Report No.: ARO–25616.1–CHS, Army Research Office, Dec. 1, 1989.

Meuzelaar, Henk L.C., et al., Characterization of Leukemic and Normal White Blood Cells by Curie–Point Pyrolysis–Mass Spectrometry, pp. 111–129, 1981, Journal of Analytical and Applied Pyrolysis.

Tas, A.C., et al., Characterization of Virus Infected Cell Cultures by Pyrolysis/Direct Chemical Ionization Mass Spectrometry, Biomedical and Environmental Mass Spectrometry, vol. 18, pp. 757–760, 1989.

Franz, et al., Clinical Recognition and Management of Patients Exposed to Biological Warfare Agents, JAMA, vol. 278, No. 5, pp. 399–411, Aug. 6, 1997, USA.

Thomas, John J., et al., Viral Characterization by Direct Analysis of Capsid Proteins, Analytical Chemistry, vol. 70, No. 18, pp. 3863–3867, Sep. 15, 1998.

Windig, W., et al., Control of the Absence of Deae–Polysaccharides in Deae–Sephadex Purified Poliovirus Suspensions by Pyrolysis Mass Spectrometry, Develop. biol Standard, vol. 47, pp. 169–177, 1981.

Holmes, Kathryn V., et al., Coronaviridae:The Viruses and Their Replication, Fundamental Virology, Third Edition, pp. 541–559, 1996, Philadelphia.

Berringer Research Limited, Biological Agent Detection by Ion Mobility Sopectrometry, Final Report CR96–012, pp. 1–25, Apr. 1996.*

Huang et al., The Journal of Biological Chemistry, 261;28:12911–12914, 1986.*

Kermasha et al., Journal of Chromatography A, 685:229–235, 1994.*

Le Cacheux et al., Applied Spectroscopy, 50:10:1253–1257, 1996.*

Ostlund et al., Journal of Mass Spectrometry, 31:1291–1296, 1996.*

Cluett et al., Journal of Cell Science, 109:2121–2131, 1996.*

Crews et al., Drug Development Research 14:31–44, 1988.*

Munoz–Barroso et al., Biochimica et Biophysica Acta 1327:17*31, 1997.*

Patzer et al., The Journal of Biological Chemistry, 253:4544–4550, Jul. 1978.*

* cited by examiner

*Primary Examiner*—Donna C. Wortman
*Assistant Examiner*—Brenda G. Brumback
(74) *Attorney, Agent, or Firm*—Holme, Roberts & Owen LLP

(57) ABSTRACT

The present invention relates to the detection of the likely presence of a virus in the environment. The detection is accomplished in a relatively rapid fashion that permits countermeasures to be taken to reduce the debilitating or deadly effects of the virus upon the target population. In one embodiment, the detection is accomplished by looking for the mass spectral signature or biomarker for a lipid, which is present in the cell cultures used to produce the virus. One biomarker that is considered particularly diagnostic for the presence of a virus is cholesterol.

12 Claims, 6 Drawing Sheets

METHOD AND APPARATUS FOR DETECTING VIRUSES USING PRIMARY AND SECONDARY BIOMARKERS

CROSS REFERENCE TO RELATED APPLICATIONS

The present application claims priority from provisional application Ser. No. 60/094,838 filed Jul. 31, 1998.

STATEMENT REGARDING FEDERALLY SPONSORED RESEARCH

The invention was made with Government support under Contract No. DAAM01-95-C0068 awarded by the Army. The Government has certain rights in the invention.

FIELD OF THE INVENTION

The present invention relates to the detection of the presence or the likely presence of a virus that has been discharged into the environment.

BACKGROUND OF THE INVENTION

Several nations and terrorist groups have or are believed to have the capability to produce chemical or biological weapons ("CBWs"). Moreover, recent events indicate that certain nations and terrorist groups are willing to use CBWs. For instance, during the war between Iraq and Iran, chemical weapons were deployed by Iraq against both Iranian ground forces and the Kurdish civilian population. An example of terrorist use of chemical weapons against a civilian population is the recent release of a nerve gas in a Tokyo subway station. One type of CBW that is of particular concern are viruses. Characteristics of the types of viruses that are believed to be particularly suitable for use in warfare and terrorist activities are: (1) a relatively short incubation period; (2) debilitating or deadly effects; and/or (3) communicability. Among the types of viruses that exhibit some or all of these characteristics are smallpox, viral encephalitides and viral hemorrhagic fevers. Among the viral hemorrhagic virus is the well-known Ebola virus. The possibility of viral agents being used against military personnel in a warfare situation or against a civilian population in a terrorist attack has created the need for rapid identification of the presence or likely presence of viral agents so that countermeasures can be taken to minimize the effects upon the target population.

SUMMARY OF THE INVENTION

The present invention makes use of the discovery that certain biochemicals (known as biomarkers) associated with viruses are susceptible to rapid detection that permits countermeasures to be taken to reduce the impact of the virus upon the target population.

Briefly, viruses are propagated by infecting host animal cells with a virus. The virus within a host cell uses the resources and environment of the host cell to reproduce. At some point, the viruses produced within a cell rupture the cell wall and move on to infect other cells and repeat the process.

To mass produce a virus, a cell culture is provided that includes host animal cells and certain chemicals that are used to nurture the host cells. The virus is introduced into the cell culture and promptly invades the host cells and begins reproducing. When enough of the virus has been produced, the virus is harvested from the cell culture. Typically, the harvesting collects the virus as well as some or all of the cell culture constituents. The harvested material can be purified. However, purification may degrade the virus and thereby decrease its virulence. Consequently, it is anticipated that any viruses released in a warfare or terrorist situation will be released in an unpurified form that includes components of the cell culture.

The present invention has identified biomarkers associated with the cell culture that can be rapidly detected. More specifically, biomarkers associated with: (1) the animal cells (typically mammalian or bird cells) that are the host cells for the virus and (2) blood serum, which provides the host cells with nutrients and growth factors, are susceptible to rapid identification. While animal cells, such as mammalian and bird cells, are a necessary part of the cell culture, blood serum may or may not be part of the cell culture. A biomarker associated with both mammalian cells and blood serum that is relatively unique to the production of viruses is cholesterol. Consequently, if the virus is dispersed in an unpurified form that includes cell culture materials, cholesterol is likely to be present. Since the cholesterol is associated with the cell culture materials rather than the virus itself, the cholesterol is considered a secondary biomarker. However, in reproducing, the virus acquires cholesterol from the host cells. In this case, cholesterol is considered a primary biomarker because it is part of the virus itself. Since cholesterol is present in the virus itself, rapid detection of the virus is possible even if the virus is dispersed in a purified form in which most or all of the cell culture constituents have been removed.

Other biomarkers that are also indicative of animal cells, including mammalian or bird cells, and blood serum are certain fatty acids. These fatty acids include, among others, palmitic, stearic, oleic and linoleic fatty acids. The detection of fatty acids can be used to further confirm the presence of a virus whose presence is already considered likely based upon the detection of another biomarker, like cholesterol.

Rapid detection of the cholesterol biomarker is possible because the mass spectrum of cholesterol is very distinct relative to the other biomarkers associated with a virus, whether in a purified or unpurified form. Mass spectrometry is a method of chemical analysis that uses the mass of a substance to identify the substance. To elaborate, associated with every type of molecule is a mass spectrum, a kind of "fingerprint", that is relatively unique to each particular molecule. The chemical analysis of an unknown substance by mass spectrometry involves obtaining a mass spectrum for the substance and comparing the mass spectrum to a library of mass spectra for known substances to identify the chemical components of the unknown substance.

The present invention involves sampling an atmosphere and performing a mass spectrum analysis of the sampled atmosphere to determine if a biomarker indicative of the presence of a virus is present. As previously noted, the present invention utilizes a biomarker that is associated with the cell culture media which is used to produce the virus in quantity, such as cholesterol. If such a biomarker is present, then it is likely that a viral agent is also present and an alarm is issued. The mass spectrum analysis is performed with a few minutes of sampling and, as such, is likely to provide sufficient warning for counter measures to be taken by at least a portion of the target population. While it is expected that viral agents used in warfare and terrorist situations will be dispersed in the atmosphere as aerosols, it is believed that the invention is adaptable to detecting viruses that are dispersed in the water.

In one embodiment, the sampling of the atmosphere is done in a fashion that presents or reduces the possibility that the mass spectrometer's time is used to analyze particles in the atmosphere that are not likely to be viruses. To elaborate, aerosolized viruses in aerosolizing media have an idealized upper limit on their size of approximately 10 microns. Consequently, sampling is done so as to avoid the sampling of particles in the atmosphere that are greater than 10 microns in size. In one embodiment, this is accomplished with a device known as a virtual impactor.

The sampling of the atmosphere is also preferably done so as to heat the sampled atmosphere to distill the biomarkers, such as cholesterol, from the sample and thereby facilitate the mass spectrum analysis. In one embodiment, heating of the sampled atmosphere is accomplished with a pyrolysis device.

To prevent tampering that could reduce the effectiveness of the invention, one embodiment employs a stand-alone power source as either a primary or secondary power source. Relatedly, the intake port for sampling the atmosphere is positioned so as to be difficult to detect and/or to plug.

DETAILED DESCRIPTION

Figure 1:
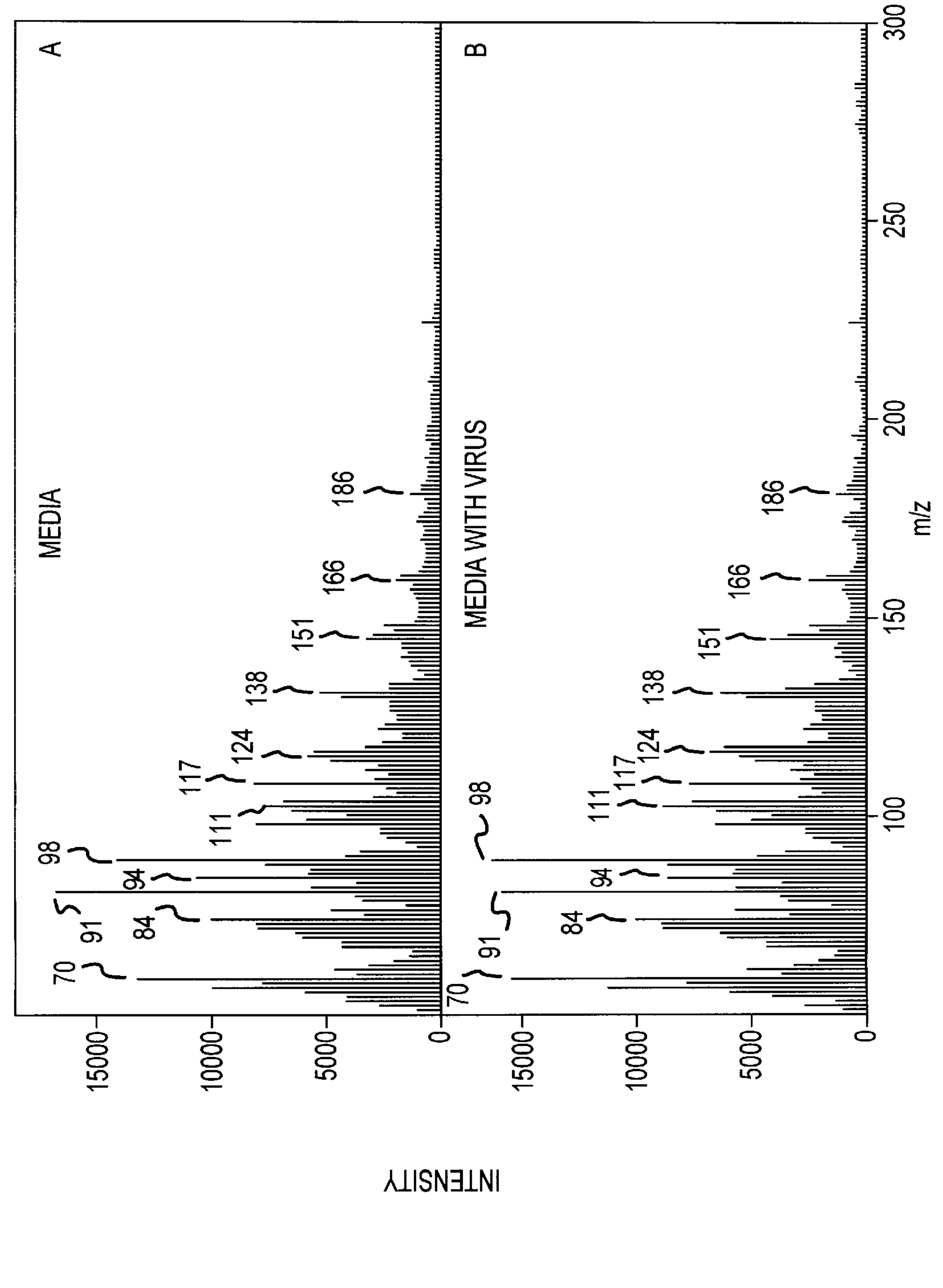
FIGS. 1A and 1B respectively show the mass spectrums for a feline kidney cell culture ("CRFK") and a CRFK cell culture inoculated with feline enteric coronavirus ("FECV")

It is believed that in warfare and terrorist situations viruses will be dispersed in an unpurified form that includes components of the cell culture in which the virus was propagated. The unpurified form requires less processing and is likely to be more virulent than a purified form. However, it has been discovered that the mass spectrum associated with a cell culture that has been contaminated with a virus is very similar to the mass spectrum associated with a pure cell culture uncontaminated by a virus. For example, FIGS. 1A and 1B respectively illustrate the mass spectrums for feline kidney cell culture ("CFRK) and CRFK inoculated with feline enteric coronavirus ("FECV"). Analysis of the two spectrums indicates that the portion of the spectrum that is most detectable based upon intensity lies in a range between 0 m/z and about 200 m/z. However, further analysis indicates that within the noted range, the two spectrums are very similar. This similarity indicates that in the high intensity range below 200 m/z, the spectrum directly attributable to the virus is overwhelmed by the spectrum associated with the chemical constituents of the cell culture. This, in turn, makes detection of the spectrum that is directly associated with the virus and in the most intense portion of the spectrum difficult. Relatedly, this difficulty in directly detecting a virus is yet another reason to believe that in warfare and terrorist situations, viruses are likely to be dispersed in an impure form.

Due to the difficulty in detecting the spectrum of a virus in the high intensity range below about 200 m/z, the indirect detection of a virus based upon the presence of cell culture constituents was investigated. A typical cell culture for propagating viruses includes the host mammalian or bird cells that are inoculated with the virus and the media for growing and maintaining the host cells. The media typically includes essential amino acids for protein synthesis, salts for pH and electrolyte control, carbohydrates for providing energy, vitamin cofactors for maintaining enzymatic functions, a chemical indicator for monitoring pH, and antibiotics for inhibiting bacterial contamination. Another common constituent of the cell culture media is blood serum, which provides additional nutrients and growth factors to the host cells.

It was found that the mass spectrums of many of the cell culture constituents were not individually reliable enough to use in indirectly detecting the presence of a virus in the environment. Specifically, the spectrums associated with the essential amino acids, salts, carbohydrates, vitamin cofactors chemical indicator and antibiotic were concentrated in the complicated spectral range below about 200 m/z. The spectrums associated with the vitamins, chemical indicator and antibiotics were found, due to their low concentrations, to be negligible.

Figure 2:
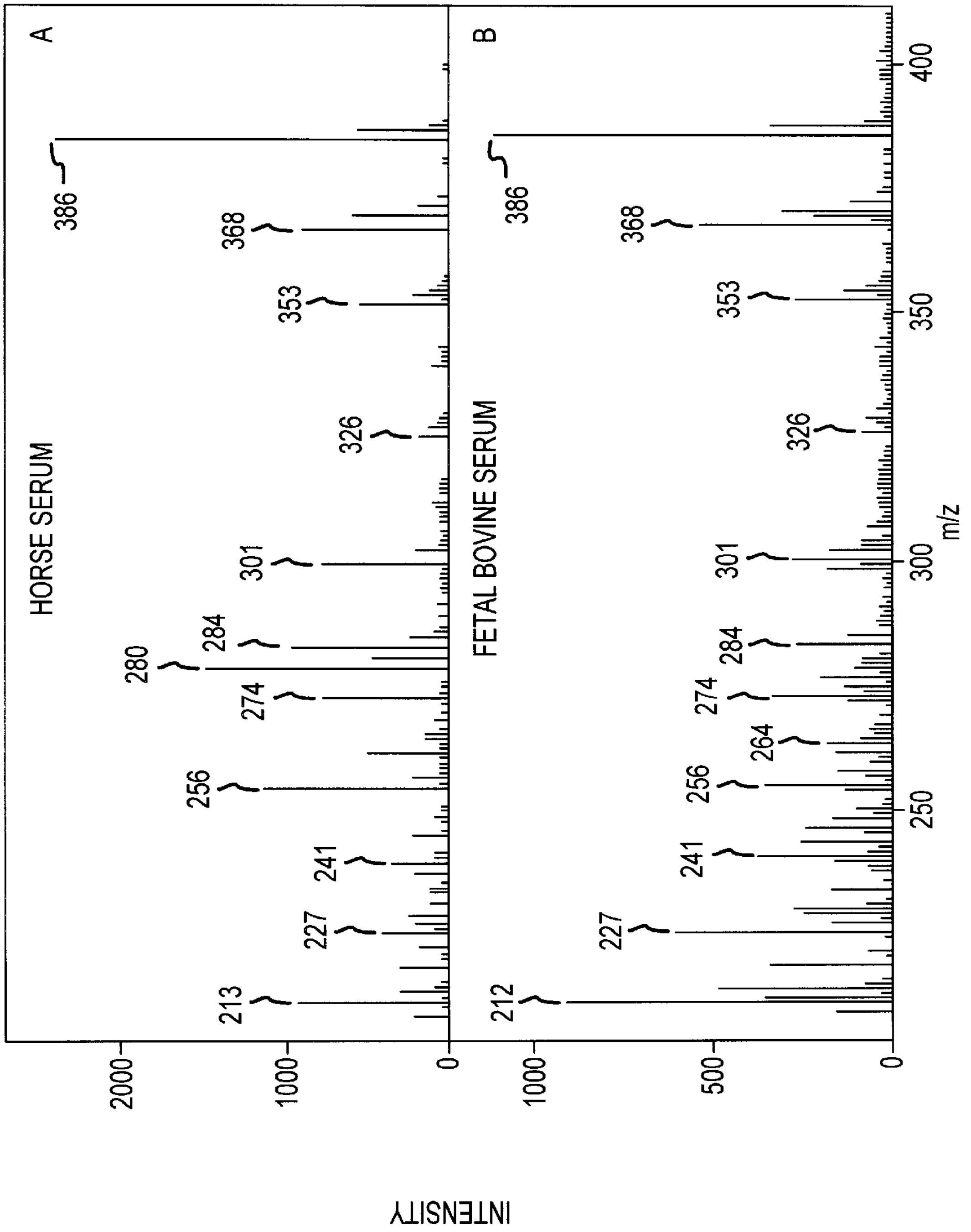
FIGS. 2A and 2B respectively show the mass spectrums above 200 m/z for horse serum and fetal bovine serum.

However, the spectrum produced by blood serum was found to be very distinct in the range above 200 m/z. In this range, the mass spectrums associated with cholesterol and palmitic, stearic, oleic and linoleic fatty acids are clearly present. For example, FIGS. 2A and 2B respectively illustrate the spectrums for horse serum and fetal bovine serum. Present in both of these spectrums are the mass spectral peaks for electron ionization molecular and fragmented ions for cholesterol (m/z 386,368,326, 301, 274, 255, 231 and 213), palmitic acid (m/z 256, 227 and 213), stearic acid (284, 255, 241, 227, 222, 213), oleic acid (m/z 282, 264, 235 and 221), and linoleic acid (m/z 280, 262, 223 and 210). The mass spectrum for animal cells, such as mammalian and bird, (eukaryotic) host cells also bear a similar spectrum above 200 m/z.

Figure 3:
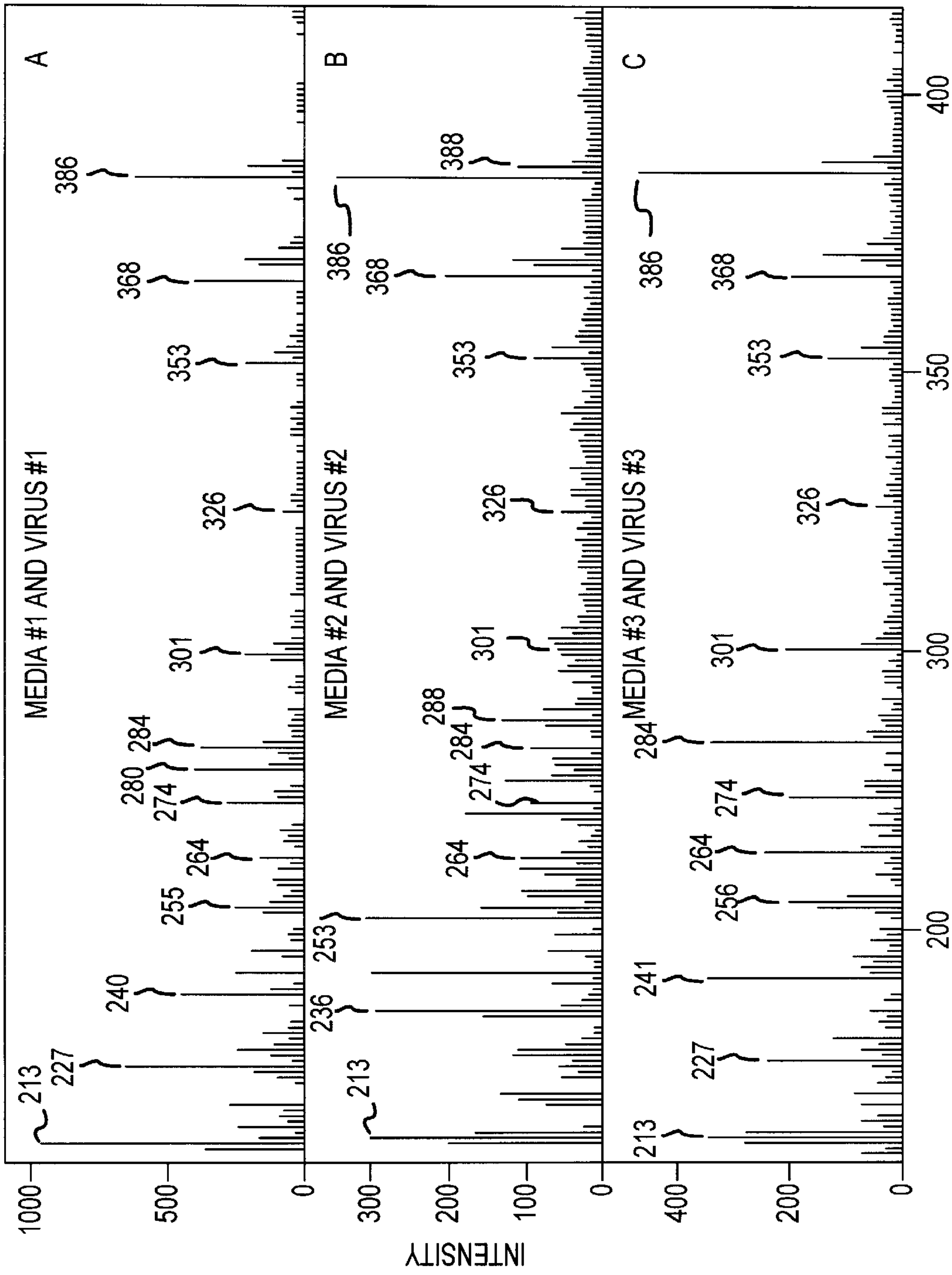
FIGS. 3A, 3B and 3C respectively show the mass spectrums above 200 m/z for CRFK cell culture media used to propagate FECV, a mouse fibroblast cell culture media used to propagate mouse hepatitis virus, and Vero cell culture media used to propagate Venezuelan Equine Encephalitis virus.
Figure 4:
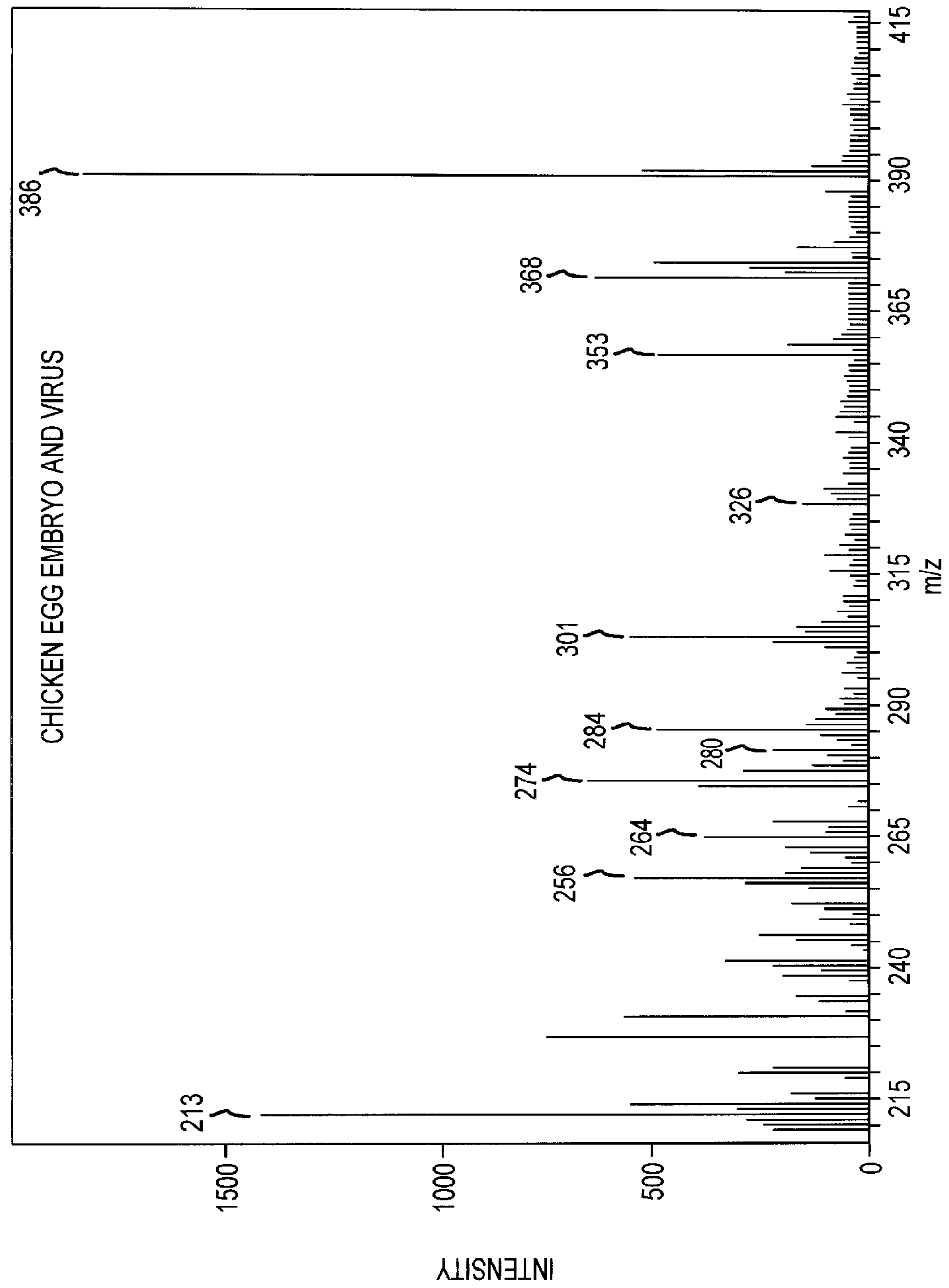
FIG. 4 shows the mass spectrum above 200 m/z for the allantoic fluid from a chicken egg embryo infected with influenza A virus.

It was found that the mass spectrums above 200 m/z for cholesterol and the noted fatty acids remain distinct even in the presence of a virus. For example, FIGS. 3A–3C illustrate the mass spectrums above 200 m/z for three different cell cultures that have each been inoculated with a different virus. Specifically, FIG. 3A is the mass spectrum for CRFK inoculated with FECV; FIG. 3B is the mass spectrum for mouse fibroblast cell culture inoculated with mouse hepatitis virus; and FIG. 3C is the mass spectrum for Vero cell culture inoculated with Venezuelan Equine Encephalitis virus. The distinctive mass spectral peaks associated with cholesterol and one or more of the noted fatty acids are present in each of the three spectrums. The cholesterol/fatty acid "fingerprint" was also present in the spectrum above 200 m/z for chicken egg embryo infected with Influenza A virus, a virus that affects humans.

Cholesterol and/or the noted fatty acids are biomarkers for the presence of animal cells (typically mammalian/bird cells) and/or blood serum used in the cell culture to propagate a virus. Consequently, detecting the presence of one or more of these secondary biomarkers is an indication that a virus in an impure form is present. The cholesterol biomarker has the further advantage of being useful in distinguishing between viral and most bacterial cell culture constituents because cholesterol is present in the animal cells, such as the host mammalian/bird cells and blood serum, used to propagate a virus but not in the constituents of the cultures used to propagate bacterium, i.e. prokaryotic cultures. A blood agar is used to propagate a small percentage of the known types of bacteria, including Haemophilus species, *Neisseria meningitidis* and *Neisseria gonorrhoeae.* Further, the only known type of bacteria in which cholesterol is incorporated into the bacteria itself are mycoplasmas.

Figure 5:
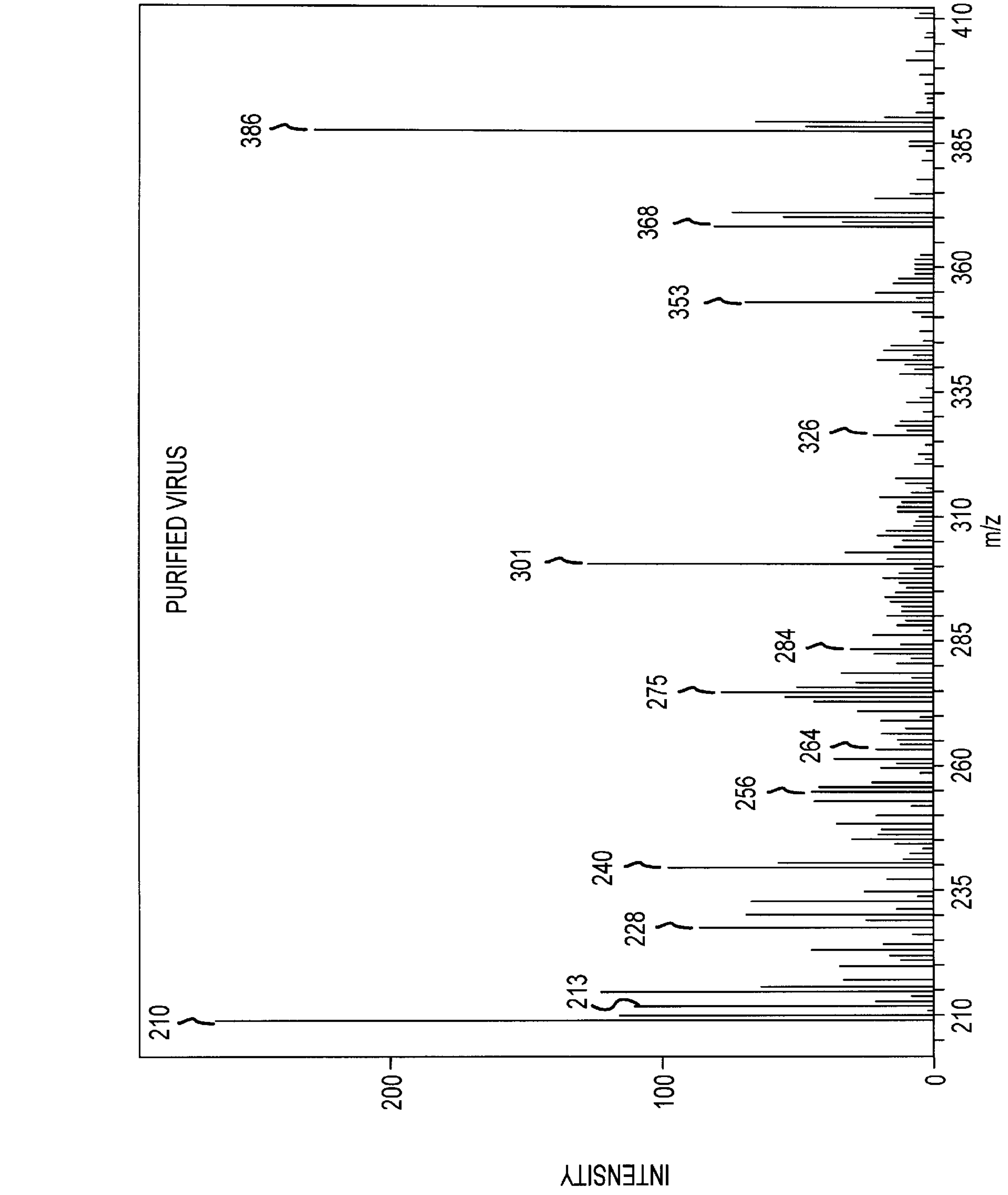
FIG. 5 shows the mass spectrum above 200 m/z for purified mouse hepatitis virus.

The possibility that a virus could be dispersed in a purified form, i.e. substantially free of any of the constituents of the cell culture used to propagate the virus, was also investigated. Again, it was found that cholesterol and/or noted fatty acids are also present in purified viruses. For example, FIG. 5 show that the mass spectral peaks associated with cholesterol and one or more of the fatty acids are present in the mass spectrum above 200 m/z for mouse hepatitis virus. It is known that the cholesterol and fatty acids result from the incorporation of the host cell's lipid membrane into the virus during the budding and release of virion into the extracellular space. In this case, the cholesterol and fatty acids are primary biomarkers because the cholesterol and fatty acids are a part of the virus.

Figure 6:
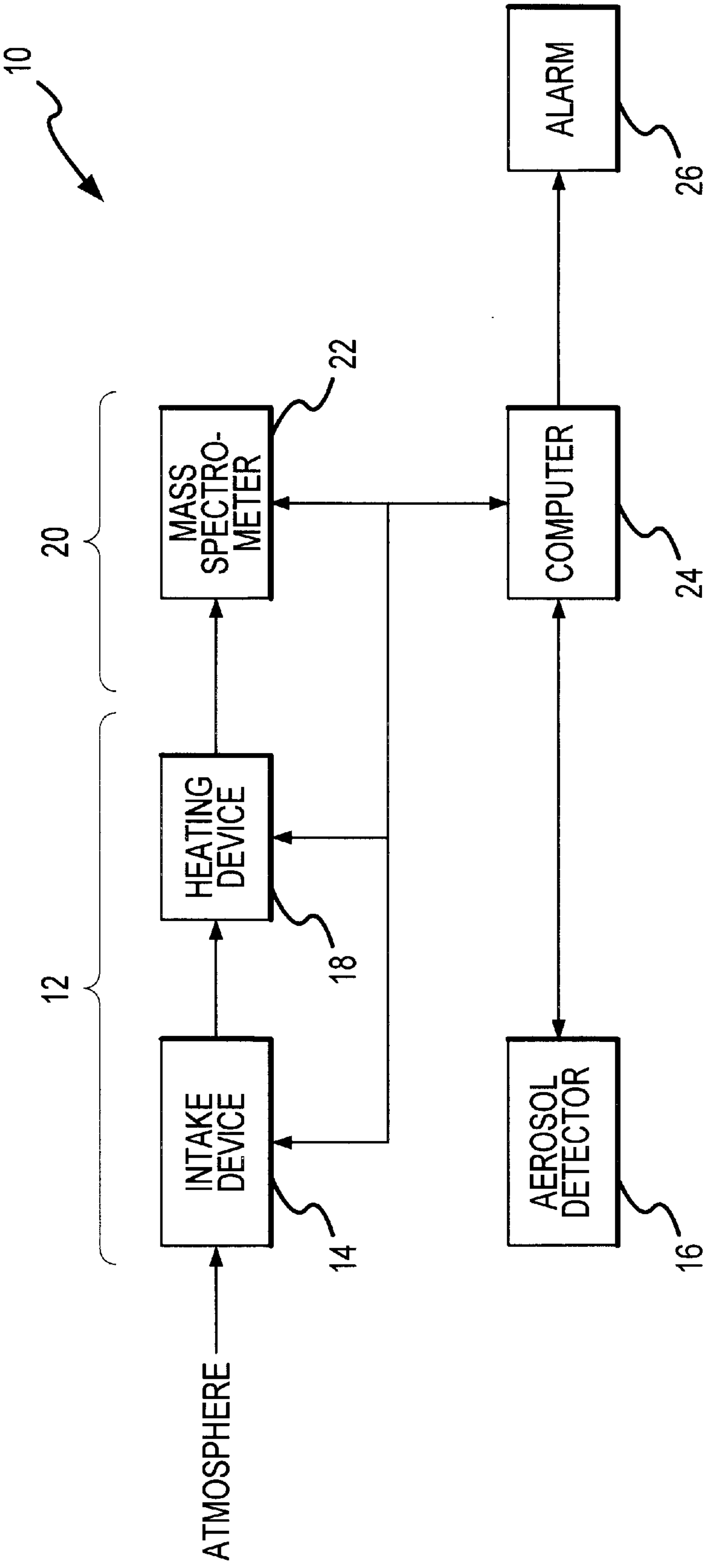
FIG. 6 illustrates a system suitable for rapid detection of viruses that have been released into the environment.

With reference to FIG. 6, a virus detection device 10 for use in detecting the likely presence of a virus in the environment is discussed. The device 10 includes a sampling section 12 for sampling the atmosphere. The sampling section 10 includes an intake device 14 for receiving the sample. In one embodiment, the intake device 14 is a virtual impactor that separates particles of a size in the range of an aerosolized virus (2 to 10 microns) in the sample from larger particles, like pollens.

In some cases, it is desirable to operate the device 10 only when an aerosol that may contain a virus is present. One such case is when the device is being powered by a stand-along power source, such as a battery. In such cases, the sampling section includes an aerosol detector 16 for detecting the presence of an aerosol in the atmosphere. Suitable detectors employ light scattering and laser technologies, as well as other technologies that are being used in smoke detectors and the like.

The sampling section 12 further includes a heating device 18 for distilling any cholesterol and/or fatty acids from the sample of the atmosphere received by the intake device 14. A suitable heating device is a pyrolysis device that is commonly used in mass spectrometry. However, other devices capable of providing sufficient heat to distill out the lipids are also feasible, including laser based devices.

The device 10 further includes an analysis section 20 for determining whether cholesterol and/or fatty acids that are indicative of the likely presence of a virus in the sampled atmosphere are present. The analysis section 20 includes a mass spectrometer 22 for determining the mass spectrum of the sample output by the heating device 18. Also part of the analysis section 20 is a computer 24 that: (1) receives the mass spectrum output by the mass spectrometer 22; (2) analyzes the mass spectrum to determine if cholesterol and preferably fatty acids are present; and (3) outputs a signal to an alarm if the analysis of the mass spectrum indicates the likely presence of a virus in the atmosphere. The computer 24 includes a memory with a library of mass spectrums for cholesterol and the noted fatty acids. The computer 24 determines if cholesterol and fatty acids are present by comparing the mass spectrum received from the mass spectrometer 22 to the stored mass spectrums for cholesterol and the fatty acids.

While the presence of cholesterol is diagnostic of the likely presence of a virus in the atmosphere and the presence of one or more of the fatty acids a further confirmation of the presence of a virus, further confirmation is possible using the mass spectrums associated with the other constituents of the cell culture. In this case, the library includes the spectrum for these other constituents.

The device 10 includes an alarm 26 that is actuated by the computer 24 if a virus is likely to be present in the environment. In most situations, the alarm 26 is an audio and/or visual alarm. One type of alarm directs members of the target population to a particular location, such as an isolation area, and/or to don protective clothing.

To prevent tampering, it is desirable that the device 10 be located in a place that is not readily accessible. In this regard, it is particularly important that the intake device 14 be relatively inaccessible to prevent the inlet of the intake device 14 from being plugged. In addition, it is desirable that the intake device 14 be difficult to detect, especially if the intake device 14 cannot be located in an inaccessible location. A stand-alone power supply, such as a battery, is also desirable as either a back-up to a conventional power supply that is subject to sabotage or a primary power source.

In operation, the device 10 commences to determine if a virus is likely to be present in the atmosphere by using the intake device 10 to sample the atmosphere. Typically, the sample is taken per the direction of the computer 24 based upon the detection of an aerosol in the atmosphere by the aerosol detector 16. If, however, the device 10 operates in a continuous mode, the computer 24 directs the intake device 10 to take samples that are processed in a pipeline fashion, i.e. samples are taken at a rate that is dictated by the slowest part of the sample processing. The sampled atmosphere is subsequently conveyed to the heating device 18 to distill any cholesterol and fatty acids present in the sample. The heated sample is then conveyed to the mass spectrometer 22 to determine the mass spectrum of the sampled atmosphere and, in particular, the mass spectrum above 200 m/z. The mass spectrum of the sampled atmosphere is conveyed to the computer 24 to determine whether primary or secondary biomarkers attributable to the cell culture are present. This is done by comparing the mass spectrum of the sample to a library of mass spectrums for lipids and, in particular, cholesterol and the noted fatty acids. If cholesterol is present, the computer 24 activates the alarm 26. However, before activating the alarm 26, the computer 24 also preferably analyzes the mass spectrum from the mass spectrometer 24 to determine if any of the noted fatty acids are present in the sampled atmosphere. If one or more of the noted fatty acids is also present, the computer 24 actuates the alarm 26. Further, confirmation of the likely presence of a virus is possible using the mass spectrums of the other constituents of the cell culture. To avoid false alarms, the spectrum from the mass spectrometer 22 can also be compared to a mass spectrum for the atmosphere under normal conditions that is retained in the library. The time elapsed between the taking of the sample and the completion of the analysis is approximately 5 minutes or less.

All types of mass spectrometers are capable of being used to detect the cholesterol and fatty acids associated with an aerosolized virus. The types of inlets and ionization techniques most readily applicable to virus detection include electrospray (ESP) ionization, MALDI, membrane introduction, electron ionization, chemical ionization and atmospheric pressure ionization.

There are also other techniques for analyzing a sample of the atmosphere to assess whether an aerosolized virus is likely to be present based upon the detection of cholesterol and preferably the detection of fatty acids. These techniques include Fourier Transform Infrared Spectroscopy (FTIR), colorimetric techniques, liquid chromatography and gas chromatography. Presently, most of these analysis techniques take 15–30 minutes, which may not provide sufficient warning to take effective countermeasures. However, the performance of these techniques (particularly, gas chromatography) have been steadily improving in recent years and may shortly have comparable performance to mass spectrometers.

The foregoing description of the invention has been presented for purposes of illustration and description. Further, the description is not intended to limit the invention to the form disclosed herein. Consequently, variations and modification commensurate with the above teachings, and the skill or knowledge in the relevant art are within the scope of the present invention. The preferred embodiment described hereinabove is further intended to explain the best mode known of practicing the invention and to enable others skilled in the art to utilize the invention in various embodiments and with the various modifications required by their particular applications or uses of the invention. It is intended that the appended claims be construed to include alternate embodiments to the extent permitted by the prior art.

What is claimed is:

1. A method for detecting the likely presence of a virus in the environment so that countermeasures can be deployed, the method comprising:

sampling the atmosphere;

analyzing the sampled atmosphere to determine if cholesterol, which is indicative of a virus, is present, wherein said step of analyzing includes subjecting the sampled atmosphere to pyrolysis to free any cholesterol present in the sampled atmosphere; and issuing, if a cholesterol is present, an alarm so that countermeasures can be deployed against the virus.

2. A method, as claimed in claim 1, wherein:

said step of sampling comprises using a laser technique to assess the presence or absence of an aerosol in the atmosphere.

3. A method, as claimed in claim 1, wherein said step of analyzing comprises:

obtaining a mass spectrum for the sample; and inspecting said mass spectrum above about 200 m/z for peaks indicative of the presence of cholesterol.

4. A method, as claimed in claim 1, wherein:

said step of analyzing comprises using gas chromatography.

5. A method, as claimed in claim 1, wherein:

said step of issuing comprises directing an individual to a particular location.

6. A method, as claimed in claim 1, wherein:

said steps of sampling and analyzing cumulatively take less that about 15 minutes.

7. A method, as claimed in claim 1, wherein:

said steps of sampling and analyzing cumulatively take no more than about 5 minutes.

8. A method, as claimed in claim 1, wherein:

said step of analyzing comprises detecting cholesterol as a primary biomarker or a secondary biomarker.

9. A method, as claimed in claim 1, wherein:

said step of sampling comprises using light scattering to assess the presence or absence of an aerosol in the atmosphere.

10. A method, as claimed in claim 1, wherein:

said step of analyzing comprises using liquid chromatography.

11. A method, as claimed claim 1, wherein:

said step of analyzing comprises using Fourier Transform Infrared Spectroscopy.

12. A method, as claimed in claim 1, wherein:

said step of analyzing comprises using colorimetry.

* * * * *